United States Patent
Yamamoto et al.

(10) Patent No.: US 7,318,798 B2
(45) Date of Patent: *Jan. 15, 2008

(54) APPARATUS AND METHOD FOR FOLDING AND TUCKING CROTCH REGION OF DISPOSABLE DIAPER

(75) Inventors: Hiroki Yamamoto, Kagawa-ken (JP); Akihisa Shiomi, Kagawa-ken (JP); Akihide Ninomiya, Kagawa-ken (JP); Takanori Yano, Kagawa-ken (JP)

(73) Assignee: Uni-Charm Co., Ltd., Shikokuchuo-shi (JP)

( * ) Notice: Subject to any disclaimer, the term of this patent is extended or adjusted under 35 U.S.C. 154(b) by 405 days.

This patent is subject to a terminal disclaimer.

(21) Appl. No.: 11/044,112

(22) Filed: Jan. 28, 2005

(65) Prior Publication Data

US 2005/0125981 A1    Jun. 16, 2005

Related U.S. Application Data

(63) Continuation of application No. PCT/JP03/10791, filed on Aug. 26, 2003.

(30) Foreign Application Priority Data

Aug. 28, 2002  (JP)  .............................. 2002-248448
Jul. 23, 2003   (JP)  .............................. 2003-200579

(51) Int. Cl.
*B31B 21/26*    (2006.01)

(52) U.S. Cl. ..................... 493/254; 493/429; 493/446; 156/164

(58) Field of Classification Search ................ 493/254, 493/429, 431, 437, 446; 156/164, 161, 204, 156/229

See application file for complete search history.

(56) References Cited

FOREIGN PATENT DOCUMENTS

| EP | 1 177 782 A1 | 2/2002 |
|----|--------------|--------|
| JP | 05-031135    | 2/1993 |
| JP | 05-031136    | 2/1993 |
| JP | 05-042180    | 2/1993 |
| JP | 3021190      | 11/1995 |
| JP | 09-131364    | 5/1997 |

*Primary Examiner*—Sameh H. Tawfik
(74) *Attorney, Agent, or Firm*—Lowe Hauptman Ham & Berner LLP

(57) ABSTRACT

An apparatus includes a first rotary disc, a plurality of folding plates mounted on a peripheral zone of the first rotary disc, a plurality of positive motion cams mounted on the peripheral zone of the first rotary disc so as to be interposed between the first rotary disc and the folding plates, a second rotary disc located on a side opposite to the first rotary disc and a plurality of auxiliary plates mounted on a peripheral zone of the second rotary disc. The folding plates and the auxiliary plates synchronously move into a contiguous diaper structure and simultaneously the guide arms move into a clearance between the guide blades so that opposite lateral zones of a crotch region may be held between the guide arms and the guide blades and thereby the crotch region may be tucked into the contiguous diaper structure.

10 Claims, 12 Drawing Sheets

APPARATUS AND METHOD FOR FOLDING AND TUCKING CROTCH REGION OF DISPOSABLE DIAPER

This application is a continuation of International Application No. PCT/JP2003/010791 filed Aug. 26, 2003, which claims priority to Japanese Application Serial Nos. 2002-248448 filed on Aug. 28, 2002 and 2003-200579 filed Jul. 23, 2003, all of which are hereby incorporated by reference herein in their entirety.

BACKGROUND OF THE INVENTION

The present invention relates to an apparatus and a method for folding and tucking disposable diapers in crotch regions inwardly of the diaper as the diaper is fed in a machine direction.

Various processes for making pull-on diapers are well known, (for example, from Japanese Laid-Open Patent Application Publications Nos. 1993-31135A, 1993-31136A and 1993-42180A). A typical example of the well-known processes will be described below.

The process comprises the steps of forming a contiguous laminated structure by interposing liquid-absorbent cores at regular intervals between a liquid-pervious continuous first web and a liquid-impervious continuous second web both running in a machine direction so that each of the liquid-absorbent cores may be arranged in a cross direction orthogonal to the machine direction, folding back the contiguous laminated structure along a center line extending in the machine direction with the second web inside, joining these webs along a heat-sealing line extending in the cross direction between each pair of the liquid-absorbent cores adjacent to each other, cutting out portions of the contiguous laminated structure along first cutting lines each being convex in the cross direction symmetrically about the center line to form leg-holes and finally cutting the contiguous diaper structure along second cutting lines each extending in the cross direction between each pair of the heat-sealing lines to obtain a plurality of individual pull-on diapers. The pull-on diaper made by such conventional process is composed of a front waist region, a rear waist region and a crotch region so as to define a waist-hole and a pair of leg-holes.

In the case of the diaper made by the process as has exemplarily been described above, the leg-holes open laterally with respect to the waist-hole which opens in a vertical direction as viewed from above with the waist-hole broadened with the hands. In other words, the waist-hole is out of linear alignment with the leg-holes and the crotch region lies right against the waist-hole. With such diaper, the wearer's toes or heels are prone to get stuck on transversely opposite side edges of the crotch region as the wearer's legs are let through the waist-hole and the leg-holes when the diaper is put on the wearer's body. In consequence, a much time may be taken to put the diaper on the wearer's body.

From the other viewpoint also, such diaper is inconvenient due to the minimum width of the crotch region usually being larger than that of the wearer's crotch region. Specifically, the crotch region of the diaper is too bulky to be properly received by the wearer's crotch region and causes the wearer to feel an incompatibility. Furthermore, the crotch region may be irregular folded and/or formed with a plurality of irregular creases as the crotch region of the diaper is squeezed between the wearer's thighs. As a result, a body discharge absorbing function expected to the diaper in the crotch region is apt to be deteriorated and body discharges may leak beyond the crotch region of the diaper.

None of the processes disclosed in the above-cited Publications includes means for folding the diaper in the crotch region and therefore the diapers made by these processes are still accompanied with the problems as have been described above.

SUMMARY OF THE INVENTION

It is an object of the present invention is to provide the apparatus and the process for folding the disposable diaper in the crotch region and thereby to solve the problems as have been described above.

According to one aspect of the present invention, there is provided an apparatus for folding and tucking crotch regions of disposable diapers comprising: a conveyor mechanism conveying contiguous diaper structure having a plurality of crotch regions arranged at regular intervals in a machine direction, a plurality of first and second waist regions lying on both sides of said crotch regions as viewed in a cross direction orthogonal to said machine direction and lying contiguous one to another in said machine direction and a plurality of leg-holes each formed between each pair of said crotch regions adjacent to each other and arranged at regular intervals in the machine direction wherein, in a course of conveyance, said contiguous diaper structure is folded along a fold in said crotch region so that said first and second waist regions are opposed to each other but spaced apart from each other; a folding mechanism serving to fold and tuck said crotch region of said contiguous diaper structure from said leg-holes lying on both sides of said crotch region toward an inside of said contiguous diaper structure; said folding mechanism including a first rotary disc located outside said fold in said crotch region as viewed in said cross direction and adapted to rotate about an axis extending in a thickness direction of said diaper structure in a direction in which said diaper structure is conveyed and a plurality of folding plates arranged on said first rotary disc in a peripheral zone of said first rotary disc at regular intervals in a circumferential direction of said first rotary disc and adapted to get near to and get away from said crotch region as said first rotary disc rotates; each of said folding plates comprising a first base and a pair of guide arms arranged in said circumferential direction of said first rotary disc and extending outward in a radial direction of said first rotary disc from said peripheral zone of said first rotary disc; and said folding plates revolving around said axis of said first rotary disc as said first rotary disc rotates, said guide arms moving forward progressively from a side of said crotch region so as to go to the inside of said diaper structure as said crotch region of said diaper structure gets near to said peripheral zone of said first rotary disc so that opposite side edges of said guide arms are pressed against transversely opposite side edges of said crotch region extending in a vicinity of said fold from outside so as to compress said opposite side edges into the inside of said contiguous diaper structure, and moving backward progressively so as to draw out of said diaper structure as said crotch region gets away from the peripheral zone of said first rotary disc.

The apparatus for folding and tucking the crotch region according to the present invention includes the following embodiments.

The guide arms can repeatedly swing back and forth in said machine direction so that distal ends of said guide arms repeatedly get near to and get away from each other and wherein said opposite side edges of said guide arms progressively get near to each other as said guide arms move forward so as to go to the inside of said diaper structure and progressively get away from each other as said guide arms move backward so as to draw out of said diaper structure.

The folding mechanism includes a plurality of positive motion cams arranged at regular intervals in said circumferential direction along the peripheral zone of said first rotary disc and rotatably mounted on said first rotary disc by means of shafts extending in said thickness direction of said diaper structure; each of said folding plates has links mounted on proximal ends of said guide arms, a rod connected to said guide arms by means of said links and a pin extending in said thickness direction of said diaper structure from an end of said rod lying aside of said first base wherein said pin is slidably inserted into an eccentric cam groove of said positive motion cam; said positive motion cams revolve about the axis of said first rotary disc as said first rotary disc rotates around its own axis, said positive motion cams makes one rotation (360° rotation) about its own axis in the peripheral zone of said first rotary disc while said first rotary disc makes one rotation (360° rotation) about its own axis, and movement of said pin along said cam groove causes said rod to move forward and backward in said cross direction and thereby causes said guide arms to swing so that said distal ends thereof repeatedly get near to and get away from each other.

The folding mechanism includes a second rotary disc located on a side opposite to said first rotary disc across said diaper structure and adapted to rotate around an axis extending in said thickness direction of said diaper structure in said direction in which said diaper structure is conveyed and a plurality of auxiliary plates mounted on said second rotary disc along a peripheral zone of said second rotary disc at regular intervals in a circumferential direction of said second rotary disc and adopted to get near to and get away from said crotch region as said second rotary disc rotates; each of said auxiliary plates comprises a second base and a pair of guide blades arranged in said thickness direction of said diaper structure and extending outward in said radial direction of said first rotary disc from the peripheral zone of said first rotary disc in which said guide blades have distal ends tapered outward in said radial direction of said first rotary disc; and said auxiliary plates revolve about said axis of said second rotary disc as said second rotary disc rotates, said guide blades move forward progressively so as to go into the inside of said diaper structure through a clearance defined between said first and second waist regions in synchronization with said guide arms as said crotch region of said diaper structure gets near to a clearance defined between said first and second rotary discs and simultaneously said guide arms move into a clearance defined between said guide blades so that said transversely opposite lateral zones of said crotch region are held between said guide arms and said guide blades and thereby tucked into said contiguous diaper structure and then said guide blades progressively get away from said diaper structure as said crotch region of said diaper structure gets away from said clearance defined between said first and second rotary discs.

The continuous diaper structure comprises a liquid-pervious continuous first web, a liquid-impervious continuous second web and a plurality of liquid-absorbent cores interposed between said first and second webs and extending in said cross direction over crotch region further into said first and second waist regions.

According to another aspect of the present invention, there is provided a method for folding and tucking crotch regions comprising the steps of: conveying a continuous diaper structure having a plurality of crotch regions arranged at regular intervals in a machine direction, a plurality of first and second waist regions lying on both sides of said crotch regions as viewed in a cross direction orthogonal to said machine direction and being continuous one to another in said machine direction and a plurality of leg-holes formed between each pair of said crotch regions adjacent to each other and arranged at regular intervals in said machine direction while folding said diaper structure along a fold in said crotch region so that said first and second waist regions are opposite to but spaced apart from each other; folding and tucking said crotch region of said continuous diaper structure into said diaper structure from said leg-openings lying on both sides of said crotch region toward an inside of said contiguous diaper structure; wherein the step of folding and tucking includes rotating a first rotary disc located transversely outside said fold extending in said crotch region as viewed in said cross direction about an axis extending in a thickness direction of said diaper structure in a direction in which said diaper structure is conveyed and making a plurality of folding plates arranged on said first rotary disc in a peripheral zone of said first rotary disc at regular intervals in a circumferential direction of said first rotary disc get near to and get away from said crotch region as said first rotary disc rotates; each of said folding plates comprising a first base and a pair of guide arms arranged in said circumferential direction of said first rotary disc and extending outward in a radial direction of said first rotary disc from the peripheral zone of said first rotary disc; and revolving said folding plates about said axis of said first rotary disc as said first rotary disc rotates, moving said guide arms forward progressively from a side of said crotch region so that said guide arms go into the inside of said diaper structure as said crotch region of said diaper structure gets near to the peripheral zone of said first rotary disc so that opposite side edges of said guide arms are pressed against transversely opposite side edges of said crotch region extending in a vicinity of said fold from outside so as to compress said opposite side edges into the inside of said contiguous diaper structure, and moving said guide arms backward progressively so that said guide arms draw out of said diaper structure as said crotch region gets away from the peripheral zone of said first rotary disc.

The method for folding and tucking the crotch region according to the present invention includes the following embodiments.

The method includes the step of swinging said guide arms back and forth repeatedly in said machine direction so that distal ends of said guide arms repeatedly get near to and get away from each other and the step of making said opposite side edges of said guide arms get near to each other progressively as said guide arms move forward so as to go to the inside of said diaper structure and get away from each other progressively as said guide arms move backward so as to draw out of said diaper structure.

The step of folding and tucking includes rotating a plurality of positive motion cams arranged at regular intervals in said circumferential direction along the peripheral zone of said first rotary disc and mounted on said first rotary disc by means of shafts extending in said thickness direction of said diaper structure; each of said folding plates having links mounted on proximal ends of said guide arms, a rod connected to said guide arms by means of said links and a pin extending in said thickness direction of said diaper structure from an end of said rod lying aside of said first base in which said pin is slidably inserted into an eccentric cam groove of said positive motion cam; revolving said positive cams about said axis of said first rotary disc as said first rotary disc rotates around its own axis, rotating said positive motion cams once (360° rotation) about its own axis in the peripheral zone of said first rotary disc while said first rotary disc makes one rotation (360° rotation) about its own axis, and moving said pin along said cam groove which causes said rod to move forward and backward in said cross direction and thereby causes said guide arms to swing so that said distal ends thereof repeatedly get near to and get away from each other.

The step of folding and tucking includes conveying a second rotary disc located on a side opposite to said first rotary disc across said diaper structure and adapted to rotate around an axis extending in said thickness direction of said diaper structure in said direction in which said diaper structure and making a plurality of auxiliary plates mounted on said second rotary disc along a peripheral zone of said second rotary disc at regular intervals in a circumferential direction of said second rotary disc get near to and draw away from said crotch region as said second rotary disc rotates; each of said auxiliary plates comprising a second base and a pair of guide blades arranged in said thickness direction of said diaper structure and extending outward in said radial direction of said first rotary disc from the peripheral zone of said first rotary disc in which said guide blades have distal ends tapered outward in said radial direction of said first rotary disc; and revolving said auxiliary plates about the axis of said second rotary disc as said second rotary disc rotates, said guide blades move forward progressively so as to go to into the inside of said diaper structure through a clearance defined between said first and second waist regions in synchronization with said guide arms as said crotch region of said diaper structure gets near to a clearance defined between said first and second rotary discs and simultaneously said guide arms move into a clearance defined between said guide blades so that said transversely opposite lateral zones of said crotch region are held between said guide arms and said guide blades and thereby tucked into said contiguous diaper structure and then said guide blades progressively get away from said diaper structure as said crotch region of said diaper structure gets away from said clearance defined between said first and second rotary discs.

DETAILED DESCRIPTION OF THE PREFERRED EMBODIMENTS

Details of the apparatus and the process according to the present invention for folding the disposable diaper in the crotch region will be more fully understood from the description given hereunder with reference with to accompanying drawings.

Figure 1:
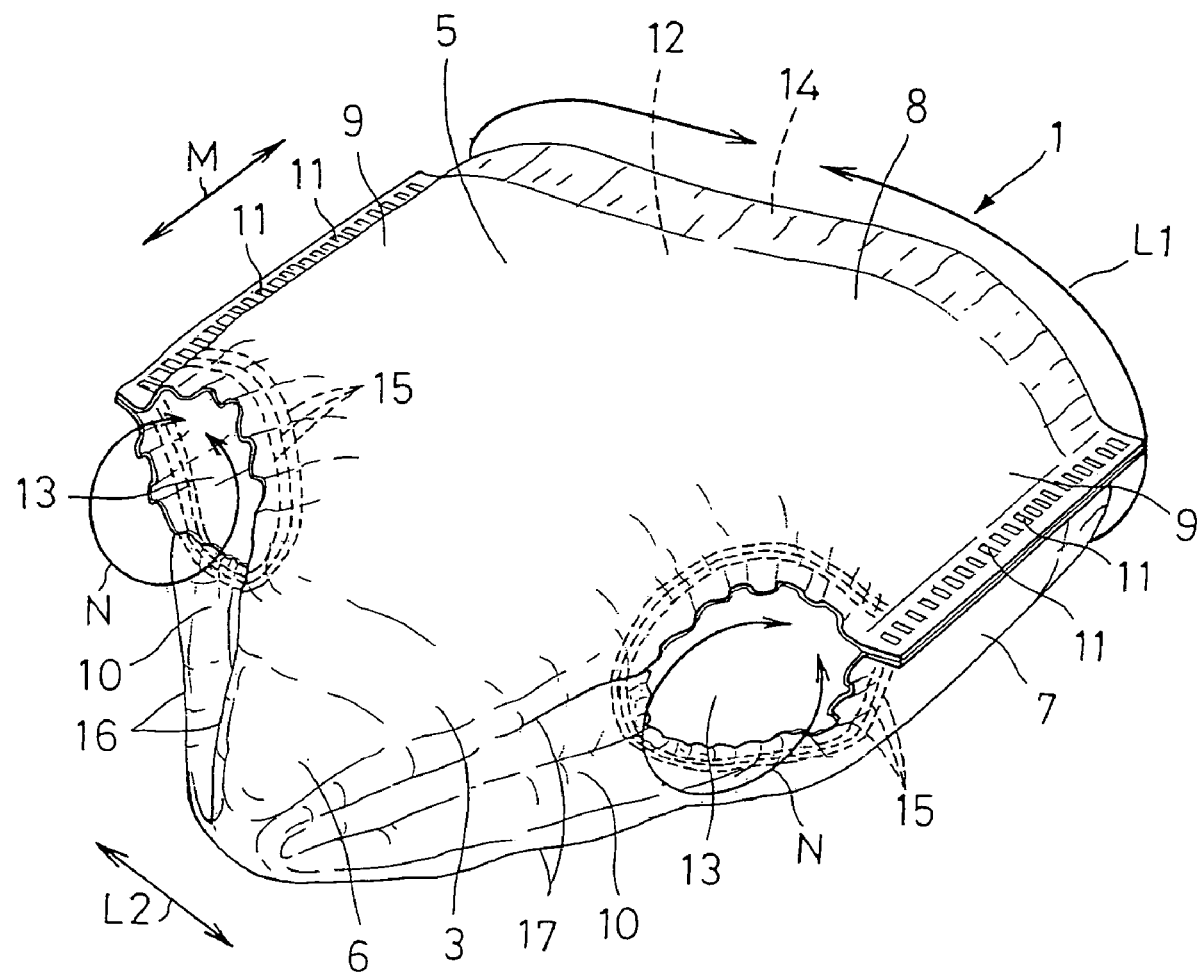
FIG. 1 is a perspective view showing an example of a pull-on diaper.
Figure 2:
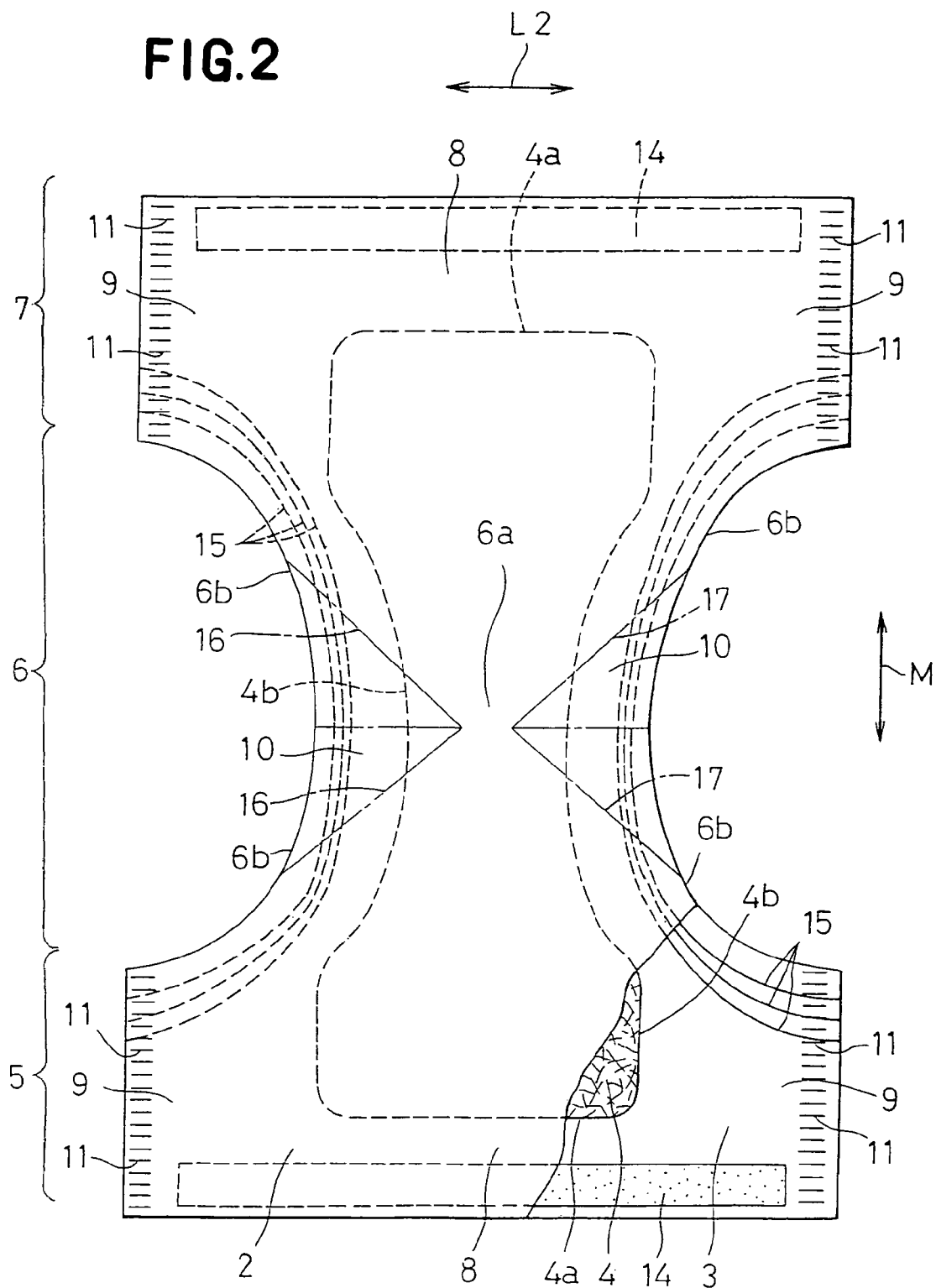
FIG. 2 is a partially cutaway developed plan view showing the diaper of FIG. 1.
Figure 3:
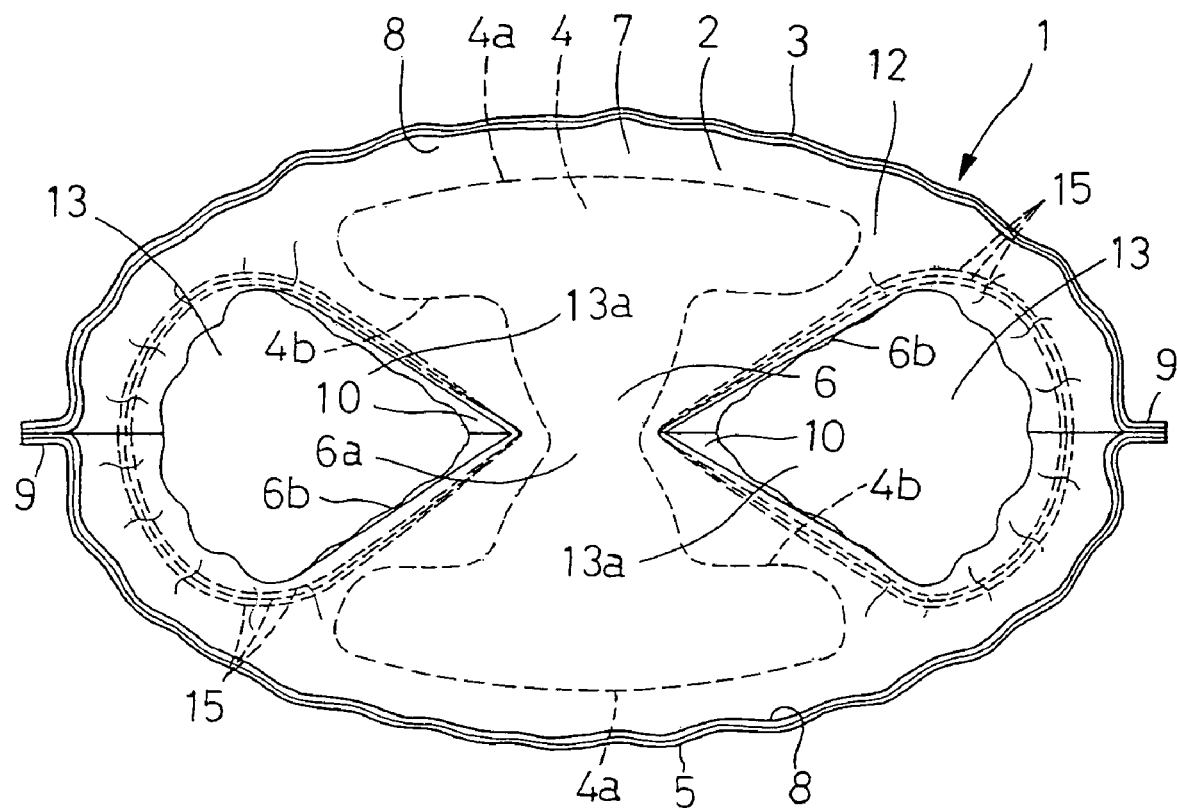
FIG. 3 is an overhead view showing the diaper of FIG. 1 from above the waist-hole.

FIG. 1 is a perspective view of a pull-on disposable diaper 1 which is folded in a crotch region 6 by an apparatus 20 as will be described later, FIG. 2 is a partially cutaway developed plan view of the diaper 1 having front and rear waist regions 5, 7 disconnected from each other along transversely opposite lateral zones 9 thereof and unfolded and FIG. 3 is an overhead view showing the diaper 1 from above a waist-hole 12. In FIGS. 1 and 2, a waist-surrounding direction is indicated by an arrow L1 (in FIG. 1 alone), a transverse direction is indicated by an arrow L2, a longitudinal direction is indicated by an arrow M and a leg-surrounding direction is indicated by an arrow N (in FIG. 1 alone).

The diaper 1 comprises a liquid-pervious topsheet 2 (first web) facing a wearer's body, a liquid-impervious backsheet 3 (second web) facing away from the wearer's body and a liquid-absorbent core 4 interposed between the top- and backsheets 2, 3 and attached to at least one of these sheets 2, 3.

The diaper 1 is composed of a front waist region 5 (first or second waist region 71, 73), a rear waist region 7 (first or second waist region 71, 73) and a crotch region 6 (crotch region 72) extending between these waist regions 5, 7. The diaper 1 has longitudinally end zones 8 of the front and rear waist regions 5, 7 extending outside longitudinally opposite ends 4a of the core 4 in the waist-surrounding direction, transversely opposite lateral zones 9 of the respective waist regions 5, 7 extending outside transversely opposite side edges 4b of the core 4 in the longitudinal direction, and transversely opposite lateral zones 10 (opposite lateral zones) of the crotch region 6 destined to surround the wearer's thighs extending outside the side edges 4b of the core 4 in the leg-circumferential direction. The core 4 extends almost entirely over the crotch region 6 and further extends into the front and rear waist regions 5, 7.

In the diaper 1, the lateral zones 9 of the respective waist regions are overlaid and joined together by means of a plurality of heat-sealing lines 11 arranged intermittently in the longitudinal direction. The diaper 1 is formed with a waist-hole 12 and a pair of leg-holes 13 lying below the waist-hole 12. In the crotch region 6, the lateral zones 10 curve so as to be convex inwardly of the diaper 1. The diaper 1 has a transverse dimension smaller in the crotch region 6 than those in the front and rear waist regions 5, 7 so as to have a substantially hourglass-like planar shape in its developed state.

The end zones 8 are provided with band-like elastically stretchable members 14 extending in the waist-circumferential direction attached thereto, respectively, in a stretched state. The lateral zones 10 are provided with a plurality of elastic members 15 attached thereto, respectively, in a stretched state. Along the end zones 8 and the lateral zones 9, 10, the top- and backsheets 2, 3 are overlaid and intermittently joined together.

As will be seen in FIG. 2, the crotch region 6 is formed with a pair of first folding guide lines 16 and a pair of second folding guide lines 17. The first folding guide lines 16 obliquely extend from a central zone 6a of the crotch region 6 to its one side edge 6b put aside toward the front and rear waist regions 5, 7, respectively so as to form a V-shape and the second folding guide lines 17 also obliquely extend from the central zone 6a of the crotch region 6 to its other side edge 6b put aside toward the front and rear waist regions 5, 7 to form a V-shape.

The lateral zones 10 in the crotch region 6 are folded inward in the transverse direction of the diaper 1 along the first and second folding guide lines 16, 17 to tuck these lateral zones 10 inward of the diaper 1. In the crotch region 6, these lateral zones 10 thus get nearer to each other inward of the diaper 1 in the transverse direction and a dimension by which these lateral zones 10 are spaced apart from each other is correspondingly reduced.

In the diaper 1, as will be apparent from FIG. 3, folding and tucking the lateral zones 10 in the crotch region 6 inward of the diaper 1 result in that the minimum transverse dimension of the crotch region 6 is substantially corresponds to the minimum dimension by which the lateral zones 10 are spaced apart from each other. In this way, it is possible to obtain the minimum transverse dimension of the crotch region 6 substantially corresponding to or even smaller than the transverse dimension of the wearer's crotch region.

With the diaper 1 put on the wearer's body, the crotch region 6 is properly received by the wearer's crotch region without apprehension that the wearer might experience any feeling of incompatibility. Even when the crotch region 6 is squeezed by the wearer's crotch region, there is no anxiety that the crotch region 6 might be irregularly folded or the core 4 might be formed with a plurality of irregular creases. In this way, body discharge absorbing capacity in the crotch region 6 is not deteriorated and any leakage of body discharges which is reliably avoided.

As seen in FIG. 3, the waist-hole 12 and the bottoms 13a of the respective leg-holes 13 are substantially aligned one with another in the vertical direction, i.e., the bottoms 13a of the leg-holes 13 lie right against the waist-hole 12. The diaper 1 is free from inconvenience that the wearer's toes and heels get stuck on the lateral zones 10 of the crotch region 6 as the wearer's legs are let through the waist-hole 12 and the leg-holes 13 when the diaper is put on the wearer's body. Therefore, it is not likely that a much time might be taken to put the diaper on the wearer's body.

Figure 4:
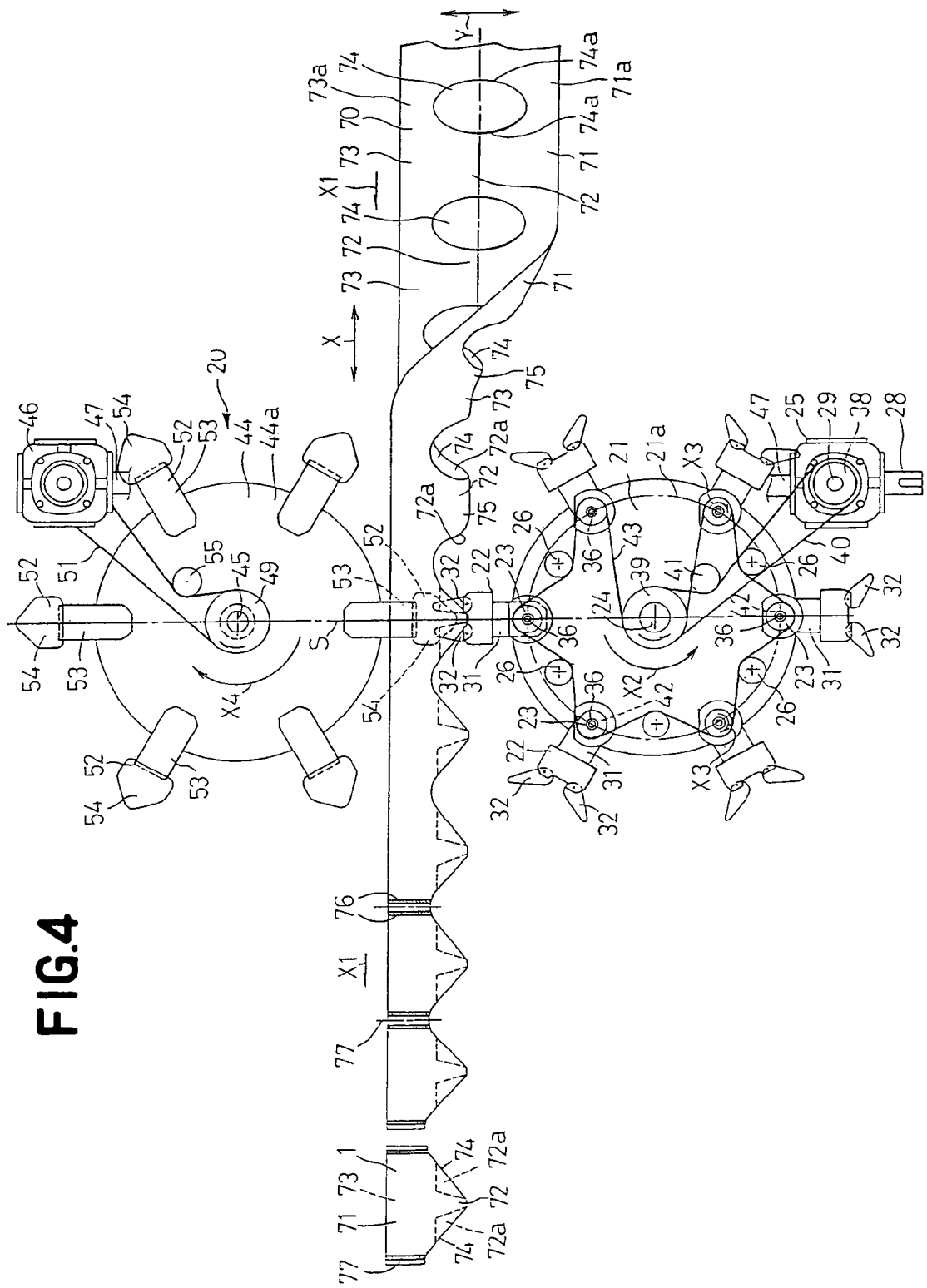
FIG. 4 is an overhead view showing an example of the apparatus for folding and tucking the crotch region.
Figure 5:
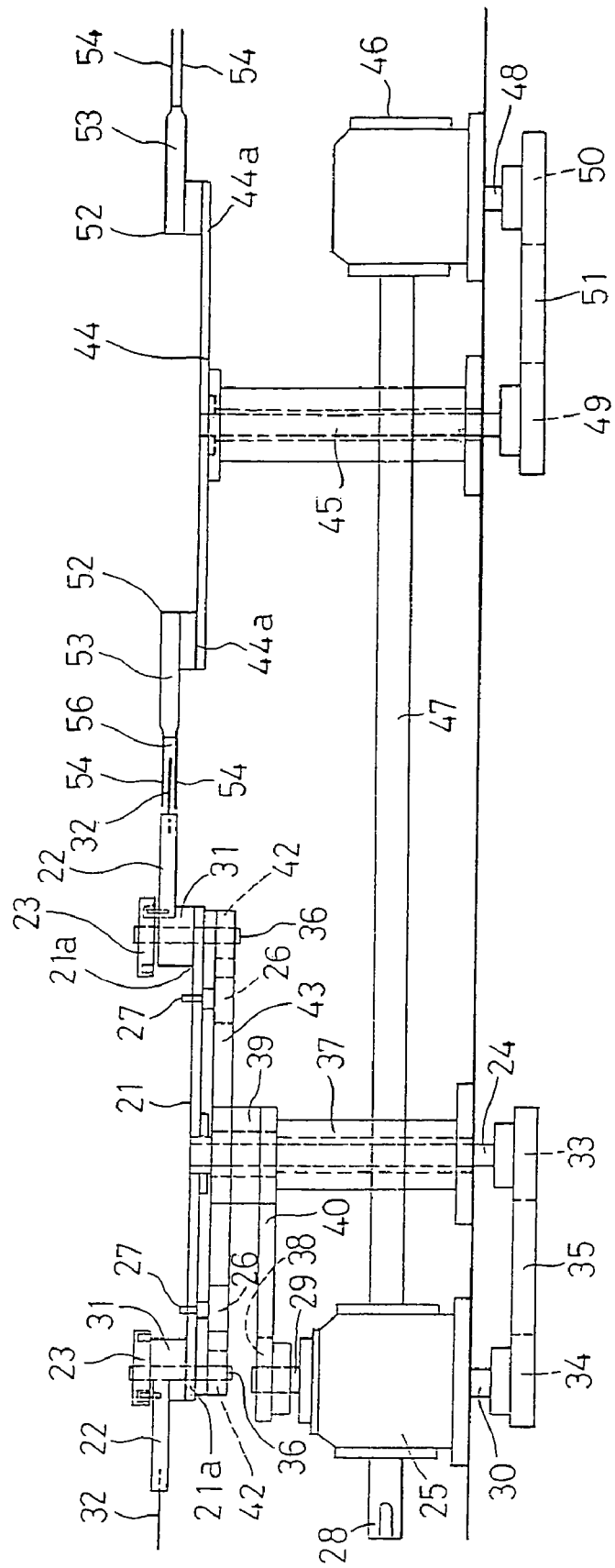
FIG. 5 is a side view showing the apparatus for folding and tucking the crotch region.
Figure 6:
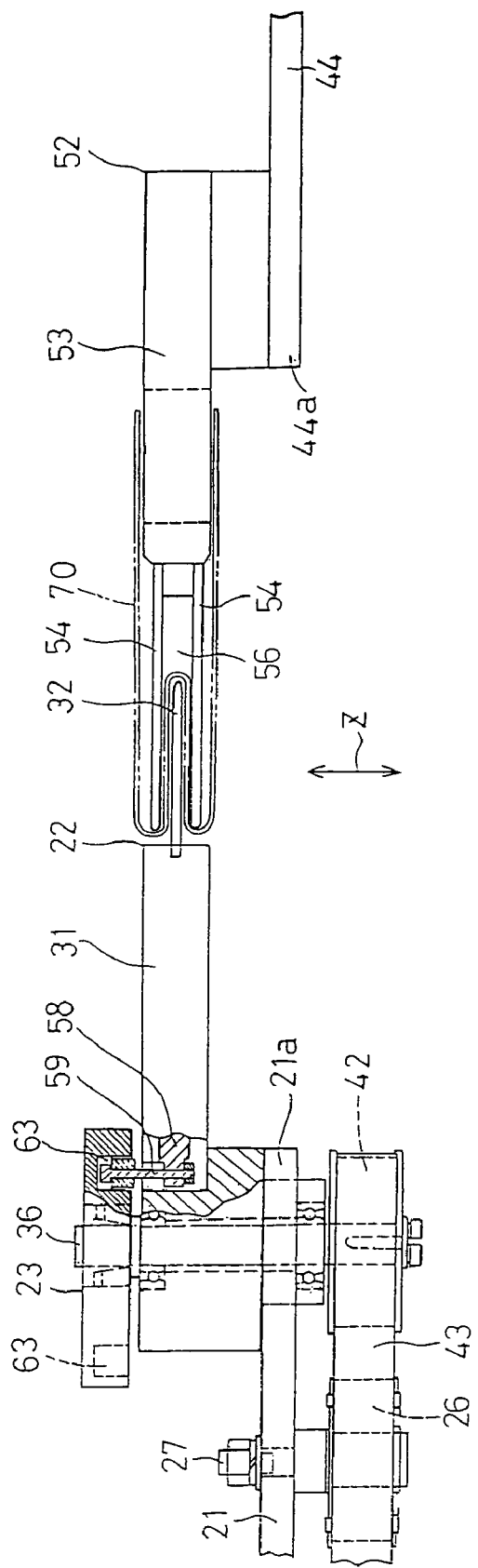
FIG. 6 is a partially cutaway scale-enlarged side view showing a part of FIG. 5.

FIG. 4 is an overhead view showing an example of the apparatus 20 for folding and tucking the crotch region, FIG. 5 is a side view corresponding to FIG. 4 showing the apparatus 20 and FIG. 6 is a partially cutaway scale-enlarged side view showing a part of FIG. 5. In FIG. 4, a machine direction is indicated by an arrow X and a cross direction orthogonal to the machine direction is indicated by an arrow Y. In FIGS. 5 and 6, a vertical direction (i.e., a thickness direction of the diaper structure 70 folded along the folding guide line 75) is indicated by an arrow Z. In FIGS. 4, 5 and 6, illustration of the contiguous diaper structure 70 is simplified so that a first web and a second web can not be distinguished from each other and, the core, the waist elastic members and the leg elastic members are not shown.

The apparatus 20 has a conveyor mechanism (conveyor means) serving to convey the contiguous diaper structure 70 at a constant speed forward in the machine direction (in the direction indicated by an arrow X1) and a folding mechanism (folding means) serving to fold down the crotch regions 72 of the contiguous diaper structure 70 into this structure 70.

The contiguous diaper structure 70 comprises a liquid-pervious continuous first web (corresponding to the liquid-pervious topsheet 2), liquid-impervious continuous second web (corresponding to the liquid-impervious backsheet 3) and a plurality of liquid-absorbent cores (corresponding to the liquid-absorbent core 4) interposed between these first and second webs and attached to at least one of these first and second webs. The contiguous diaper structure 70 has a plurality of crotch regions 72 (corresponding to the crotch region 6) arranged at regular intervals in the machine direction, a plurality of first waist regions 71 (corresponding to the front waist region 5 or the rear waist region 7) and second waist regions 73 (corresponding to the front waist region 5 or the rear waist region 7) both lying on both sides of these crotch regions 72 in the cross direction and a plurality of the leg-holes arranged at regular intervals in the machine direction each lying between each pair of the crotch regions 72 adjacent to each other. The leg-holes 74 are formed by cutting the corresponding zones away from the first and second webs and each of the leg-holes 74 has an elliptical shape having its major axis in the cross direction.

The core lies between each pair of the adjacent leg-holes 74 adjacent to each other and extends over the substantially entire crotch region 72 and further extends into the first and second waist regions 71, 73 in the cross direction. Portions of the first web and the second web extending outward beyond the peripheral edge of the core are overlaid and intermittently joined together.

Each of the leg-holes 74 is provided along its peripheral zone 74a with a plurality of elastic members (not shown) attached thereto in a stretched state. The first and second waist regions 71, 73 are provided along the longitudinal end zones 71a, 73a thereof with elastic members (not shown) extending in the machine direction attached thereto in a stretched state (See FIGS. 1 and 2).

In the diaper structure 70, the core may be provided along its both lateral zones as viewed in the machine direction with well-known leak-barrier sheets normally biased to rise above the first web. The diaper structure 70 may comprise the liquid-impervious continuous second web and a plurality of absorbent panels placed on an inner surface of the second web between the respective pairs of the leg-holes 74 adjacent to each other. In this case, each of the panels will comprise a liquid-pervious upper sheet, a liquid-impervious lower sheet and an absorbent core interposed between these upper and lower sheets.

The conveyor mechanism conveys the diaper structure 70 forward in the machine direction (in the direction indicated by the arrow X1) and, in the course of conveyance, the crotch region 72 is folded along a longitudinal fold 75 extending in the machine direction so that the first and second waist regions 71, 73 may be opposed to each other but spaced apart from each other (in a partly opened state). Though not illustrated, the conveyor mechanism comprises a guide rail along which the crotch region 72 is folded and a plurality of driving rolls adapted to rotate in a direction corresponding to the direction in which the contiguous diaper structure 70 is conveyed. The guide rail serves to fold the crotch region 72 and rotation of these driving rolls is utilized to convey the contiguous diaper structure 70.

The diaper structure 70 being conveyed forward in the machine direction is under a predetermined tension exerted thereupon in the machine direction. After the crotch region 72 has been folded along the fold 75, such tension acts on the first and second waist regions 71, 73 but substantially does not act on the crotch region 72.

The folding mechanism comprises a first rotary disc 21 located outside the fold 75 of the diaper structure 70 as viewed in the cross direction, six folding plates 22 mounted at regular intervals on the first rotary disc 21 along its peripheral zone 21a and six positive motion cams 23 overlying the respective folding plate 22, a second rotary disc 44 located on the side opposite to the first rotary disc 21 across the diaper structure 70 and six auxiliary plates 52 mounted on the second rotary disc 44 along its peripheral zone 44a.

It should be understood that the number of these folding plates 22 and the auxiliary plates 52 are not particularly specified while six folding plates 22 and six auxiliary plates 52 are exemplarily illustrated.

The first rotary disc 21 rotates in a direction (indicated by an arrow X2) corresponding to the direction in which the contiguous diaper structure 70 is conveyed about a shaft 24 extending in the vertical direction. Outside the first rotary disc 21, there is provided a gear box 25 adapted to transmit a driving force to the first rotary disc 21 and the folding plates 22. The first rotary disc 21 is provided along its peripheral zone 21a with five guide wheels 26 mounted thereon. The guide wheels 26 are located between each pair of the folding plates 22 adjacent to each other and mounted on the first rotary disc 21 by means of a shaft 27 extending in the vertical direction. These guide wheels 26 are rotatable independently of the first rotary disc 21.

A shaft 28 of the gear box 25 is rotationally driven by an electric motor (not shown). Within the gear box 25, there is provided a bevel gear (not shown) via which a rotation of the shaft 28 is transmitted to a shaft 29 extending upward from the gear box 25 in the vertical direction, a shaft 30 extending downward from the gear box 25 in the vertical direction and a shaft 47.

The folding plates 22 lie outside the fold 75 of the diaper structure 70 as viewed in the cross direction. The folding plates 22 are mounted on the first rotary disc 21 and arranged at regular intervals along its peripheral zone 21a. The folding plates 22 are movable toward and away from the crotch region 72 of the diaper structure 70 as the first rotary disc 21 rotates. Each of the folding plates 22 comprises a first base 31 and a pair of guide arms 32 extending outward from the first base 31 in a radial direction of the first rotary disc 21.

Line segments connecting the shaft 24 of the first rotary disc 21 to centers of the folding plates 22 which are adjacent to each other involve therebetween an angle of 60°. If the first rotary disc 21 is provided along its peripheral zone 21a with three folding plates 22, such angle will be 120°. If the first rotary disc 21 is provided along its peripheral zone 21a with four folding plates 22, such angle will be 90°.

The shaft 24 of the first rotary disc 21 and the shaft 30 of the gear box 25 are provided with pulleys 33, 34, respectively. These shafts 24, 30 are operatively associated with each other by means of an open belt 35 guided by the pulleys 33, 34. Rotation of the shaft 30 of the gear box 25 is transmitted to the shaft 24 of the first rotary disc 21 via the open belt 35. Rotation of the shaft 30 causes the first rotary disc 21 to rotate in the same direction (indicated by the arrow X2) as the direction in which the shaft 24 rotates.

The positive motion cams 23 overlie the first bases 31 of the respective folding plates 22 and are mounted on the first rotary disc 21 by means of shafts 36 extending in the vertical direction so that these positive motion cams 23 may be rotated independently of the first rotary disc 21. As is the case with the folding plates 22, the positive motion cams 23 are arranged at regular intervals along the peripheral zone 21a of the first rotary disc 21.

The first rotary disc 21 is provided around its bearing 37 with a pulley 39 adapted to rotate independently of the shaft 24. This pulley 39 is rotatably mounted on the bearing 37. The shaft 24 is inserted into the bearing 37. The shaft 29 of the gear box 25 is provided with a pulley 38. The shaft 29 and the pulley 39 are operatively associated with each other via open belt 40 guided by the pulleys 38, 39. Between the pulley 38 and the pulley 39, there is provided a guide wheel 41 serving to keep the belt 40 under tension. The shafts 36 of the respective positive motion cams 23 are provided with pulleys 42.

The shaft 36 is operatively associated with the pulley 39 by means of a belt 43 guided by the pulleys 39, 42. More specifically, the belt 43 extends from the pulley 39 to one of the pulleys 42 associated with one of the positive motion cams 23 and further extends, via the guide wheel 26, to the pulley 42 associated with the adjacent positive motion cam 23. Rotation of the shaft 29 is transmitted via the belt 40 to the pulley 39. Rotation of the pulley 39 is transmitted via the belt 43 to the shafts 36 of the positive motion cams 23. Rotation of the shafts 36 causes these positive motion cams 23 to rotate in a direction (indicated by an arrow X3) opposed to the direction (indicated by the arrow X2) in which the first rotary disc 21 rotates. The belt 43 is maintained under tension by the guide wheels 26.

Each pair of the guide arms 32 are opposed to each other in a circumferential direction of the first rotary disc 21. Each pair of the guide arms 32 respectively have inner side edges 32a opposed to each other in the circumferential direction of the first rotary disc 21 (See FIG. 7). The guide arms 32 are adapted to swing back and forth so that respective distal ends 32b may repeatedly get near to and get away from each other, that is, so that they repeatedly open and close to each other.

The second rotary disc 44 rotates in a direction (indicated by an arrow X4) corresponding to the direction in which the diaper structure 70 is conveyed about a shaft 45 extending in the vertical direction. Outside the second rotary disc 44, there is provided a gear box 46 adapted to transmit a driving force to the second rotary disc 44. The gear box 25 is coupled to the gear box 46 by means of a shaft 47. A rotational force is transmitted from the gear box 25 to the gear box 46 via the shaft 47. Within the gear box 46, there is provided a bevel gear (not shown) via which a rotation of the shaft 47 is transmitted to a shaft 48 extending downward from the gear box 46.

The second rotary disc 44 and the gear box 46 are provided around their shafts 45, 48 with pulleys 49, 50, respectively. The shaft 45 and the shaft 48 are operatively associated with each other by means of an open belt 51 guided by the pulleys 49, 50. Rotation of the shaft 48 is transmitted by the open belt 51 to the shaft 45 of the second rotary disc 44. Rotation of the shaft 45 causes the second rotary disc 44 to rotate in the same direction as that of the shaft 45 (in the direction X4). Between the pulley 49 and the pulley 50, there is provided a guide wheel 55 serving to maintain the belt 51 under tension.

Auxiliary plates 52 lie outside the first and second waist regions 71, 73 of the diaper structure 70. The auxiliary plates 52 are arranged at regular intervals in the circumferenctial direction along the peripheral zone 44a of the second rotary disc 44 and fixed thereon. These auxiliary plates 52 are adapted to get nearer to and draw away from the crotch region 72 through a space defined by the first and second waist regions 71, 73 opposed to each other but spaced apart from each other (i.e., in a partly opened state) of the diaper structure 70 as the second rotary disc 44 rotates. Each of these auxiliary plates 52 comprises a second base 53 and a pair of guide blades 54 extending outward from the second base 53 in a radial direction of the second rotary disc 44.

Lines segments connecting the shaft 45 of the second rotary disc 44 to centers of the second base 53 of the auxiliary plates 52 which are adjacent to each other involve therebetween an angle of 60°. If the second rotary disc 44 is provided along its peripheral zone 44a with three auxiliary plates 52, such angle will be 120°. If the second rotary disc 44 is provided along its peripheral zone 44a with four auxiliary plates 52, such angle will be 90°.

The guide blades 54 are arranged in the vertical direction and have distal ends 54a tapered from the second base 53 outward in the radial direction of the second rotary disc 44. Between these guide blades 54, a clearance 56 is defined, which has a predetermined dimension sufficient to receive the guide arm 32 of the associated folding plate 22.

The crotch region 72 of the diaper structure 70 is folded and tucked by such apparatus 20 in a manner as follows: The diaper structure 70 having the crotch region 72 folded along the fold 75 extending in the machine direction is being conveyed forward in its machine direction (indicated by the arrow X1) by the conveyor mechanism. The diaper structure 70 with the first and second waist regions 71, 73 opposed to each other but spaced apart from each other (i.e., in a partly opened state) now finds its way between the first and second rotary discs 21, 44. The first and second rotary discs 21, 44 are rotating in sync with the running speed of the diaper structure 70 in the direction corresponding to the direction in which the diaper structure 70 is conveyed (indicated by the arrow X2 and the arrow X4, respectively).

In the apparatus 20 for folding and tucking crotch regions, the guide arms 32 of the folding plates 22 progressively move into the diaper structure 70 from the side of the crotch region 72 as the crotch region 72 of the diaper structure 70 gets nearer to a clearance defined between the first and second rotary discs 21, 44. In sync with the guide arms 33 of the folding plate 22, the guide blades 54 of the auxiliary plates 52 progressively move into the diaper structure 70 through a clearance defined by the first and second waist regions 71, 73 opposed to each other but spaced apart from each other (i.e., in a partly opened state).

As the crotch region 72 of the diaper structure 70 gets nearer to an imaginary line S extending between the shafts 24, 45 of the respective rotary discs 21, 44, the opposite side edges 32a of the guide arms 32 having moved into the diaper structure 70 come in contact with the crotch region 72 from its outer side and the guide arms 32 swing inward so that the distal ends 32b of the respective guide arms 32 may get close to each other. In this way, the opposite side edges 32a of the guide arms 32 are pressed against the transversely opposite lateral zones 72a of the crotch region 72 extending in the vicinity of the fold 75 so as to compress these lateral zones 72a of the crotch region 72 into the contiguous diaper structure 70. Simultaneously, the guide arms 32 move into the clearance 56 defined between the guide blades 54 so that the lateral zones 72a of the crotch region 72 may be held between the guide arms 32 and the guide blades 54 and thereby tucked into the diaper structure 70.

In the apparatus 20 for folding and tucking crotch regions, the guide arms 32 swing so that the distal ends 32b may be spaced apart from each other as the crotch region 72 of the diaper structure 70 move away from the clearance between the first and second rotary discs 21, 44. Then, the guide arms 32 move backward progressively so as to draw out of the diaper structure 70 and, in sync with this, the guide blades 54 of the auxiliary plate 52 move backward progressively so as to draw out of the diaper structure 70. The diaper structure 70 having the crotch region 72 thus folded and tucked progressively gets away from the clearance between the first and second rotary discs 21, 44 and further moves forward in the machine direction.

In the diaper structure 70 having the crotch region 72 folded along the fold 75 extending in the machine direction, the crotch region 72 is substantially free from affection of the tension exerted upon the diaper structure 70, so the lateral zones 72a of the crotch region 72 can be easily tucked and, in addition, the diaper structure 70 can be conveyed forward in the machine direction with the crotch region 72 reliably retained in a tucked state.

After the lateral zones 72a of the crotch region 72 have been tucked inward, the first and second waist regions 71, 73 which have been opposed to each other but spaced apart from each other are now completely put flat together and then the first and second webs are joined together by means of two heat-sealing lines 76 extending in the cross direction. These heat-sealing lines 76 lie in the middle of each leg-opening 74 as viewed in the machine direction so as to extend across the first and second waist regions 71, 73 in the cross direction. Subsequently, the first and second webs are cut along cutting lines 77 each extending in the cross direction between the heat-sealing lines 76. These cutting lines 77 extend across the first and second waist regions 71, 73 in the cross direction. The contiguous diaper structure 70 is cut along the respective cutting lines 77 to obtain a plurality of the individual diapers 1 shown in FIG. 1 which are arranged side by side in the machine direction.

This apparatus 20 for folding and tucking crotch regions allows the crotch region 72 of the diaper structure 70 to be continuously and rapidly folded and tucked inward. The apparatus 20 allows the crotch region 72 to be reliably folded and tucked inward since the guide arms 32 are pressed against the lateral zones 72a of the crotch region 72 to compress these lateral zones 72a into the contiguous diaper structure 70 and simultaneously the guide arms 32 move into the clearance 56 between the guide blades 54 to hold the lateral zones 72a of the crotch region 72 between the guide arms 32 and the guide blades 54.

Figure 7:
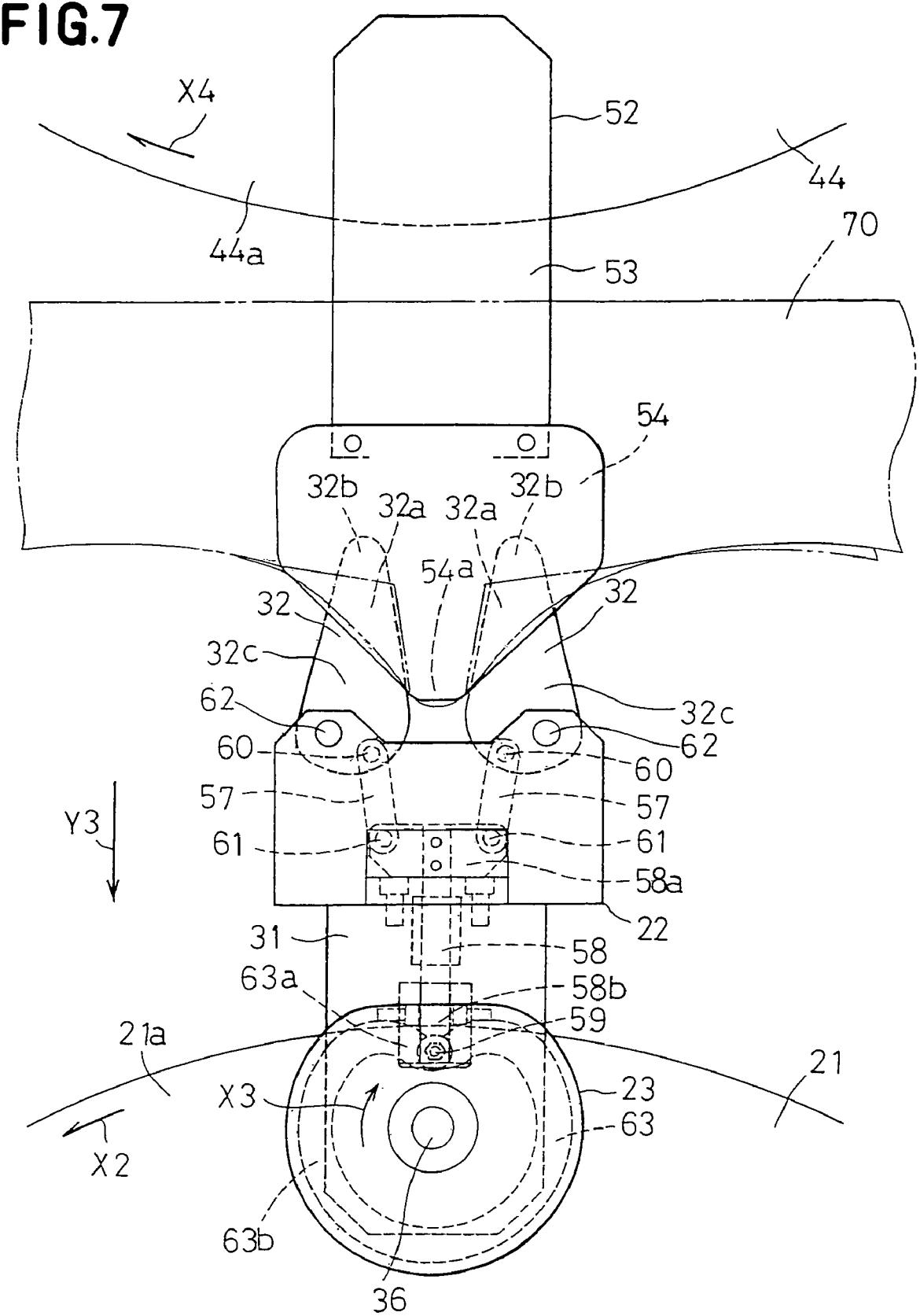
FIG. 7 is a scale-enlarged overhead view of a folding plate and an auxiliary plate.
Figure 8:
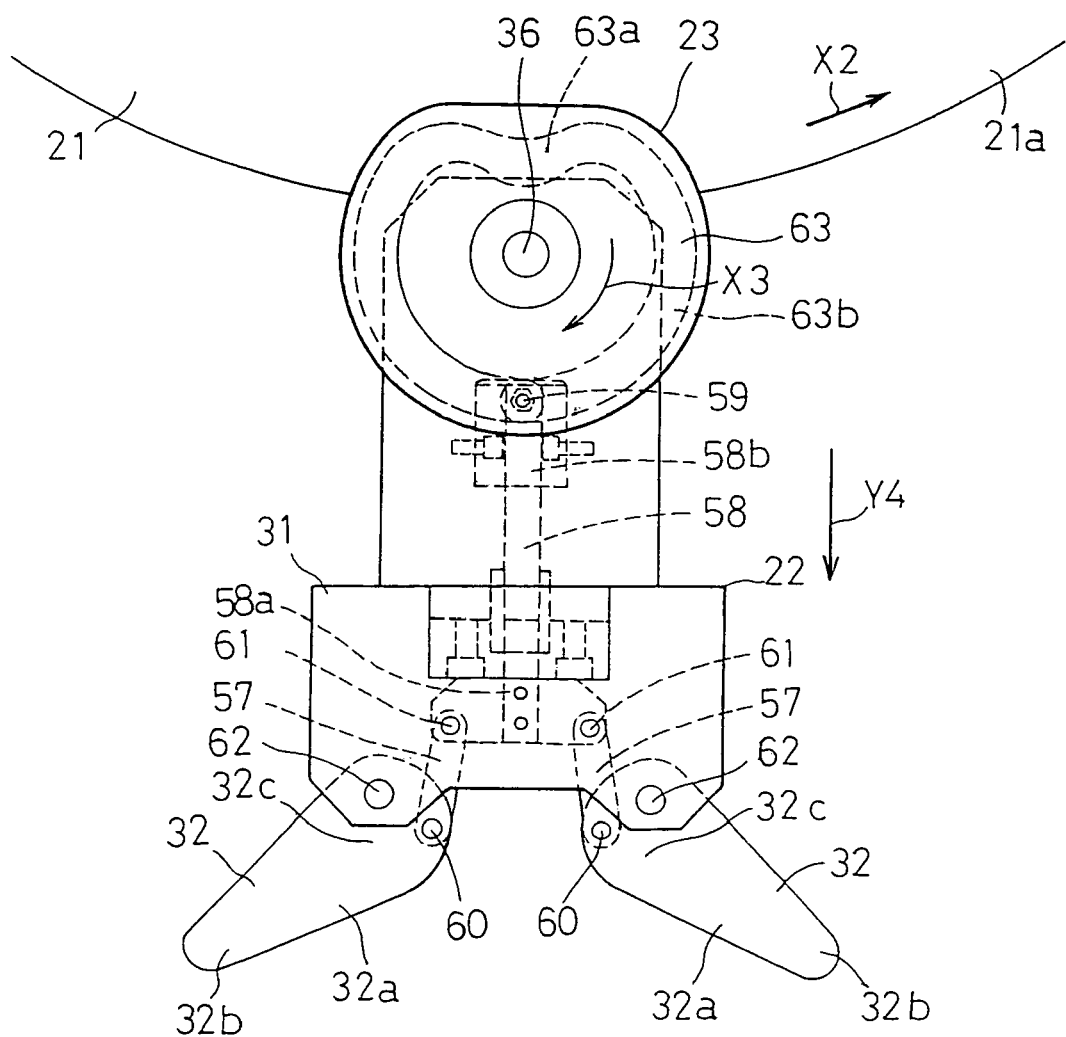
FIG. 8 is a scale-enlarged overhead view of the folding plate.

FIG. 7 is a scale-enlarged overhead view of the folding plate 22 and the auxiliary plate 52 and FIG. 8 is a scale-enlarged overhead view of the folding plate 22. In FIG. 7, the guide arms 32 are illustrated as having moved into the clearance 56 between the guide blades 54. FIG. 8 illustrates the folding plate 22 after the first rotary disc 21 has rotated from its position in FIG. 7 by 180°.

Each of the folding plates 22 has a pair of links 57 mounted on proximal end zones 32c of the guide arms 32, a rod 58 connected to the links 57 and a pin 59 extending from a rear end zone 58b (end zone) of the rod 58 in the vertical direction. The links 57 and the rod 58 extend inward in the radial direction of the first rotary disc 21 from the proximal end zones 32c of the guide arms 32. The links 57 are mounted on shafts 60 provided in the proximal end zones 32c of the guide arms 32 and on shafts 61 lying in a front end zone 58a of the rod 58. The guide arms 32 have the proximal end zones 32c mounted on the first base 31 by means of pivot pins 62.

The positive motion cams 23 respectively have eccentric cam grooves 63. The cam groove 63 includes by a depressed zone 63a sloping down toward the shaft 36 of the cam 23 and a circular zone 63b extending along a peripheral edge of the positive motion cam 23. The pin 59 is slidably inserted in the cam groove 63. Each of these positive motion cams 23 makes one rotation (360° rotation) about its own axis in the peripheral zone 21a of the first rotary disc 21 while these positive motion cams 23 revolve about the axis of the first rotary disc 21 during one rotation (360° rotation) of the first rotary disc 21 about its own axis. Rotation of the positive motion cams 23 around their own axes causes the pins 59 to move along the cam grooves 63 and thereby causes the rods 58 to move forward and backward in the cross direction. Movement of the rods 58 forward and backward causes the distal ends 32b of the guide arms 32 to be repeatedly got near to and get away from each other by means of the links 57.

When the folding plates 22 is opposed to one auxiliary plates 52 as shown in FIG. 7, the pin 59 is positioned in the zone 63a of the cam groove 63 and the rod 58 moves inward in the radial direction of the first rotary disc 21 (in the direction Y3). Movement of the rod 58 backward causes the guide arms 32 to swing by means of the links 57 so that the opposite side edges 32a of the guide arms 32 may get near to each other.

When the first rotary disc 21 rotates from its position in FIG. 7 by 180°, the pin 59 is positioned in the zone 63a of the cam groove 63 and the rod 58 moves outward in the radial direction of the first rotary disc 21 (in the direction Y4). As of the rod 58 moves the guide arms 32 to swing by means of the links 57 so that the opposite side edges 32a of the guide arms 32 may be drawn away from each other.

Figure 9:
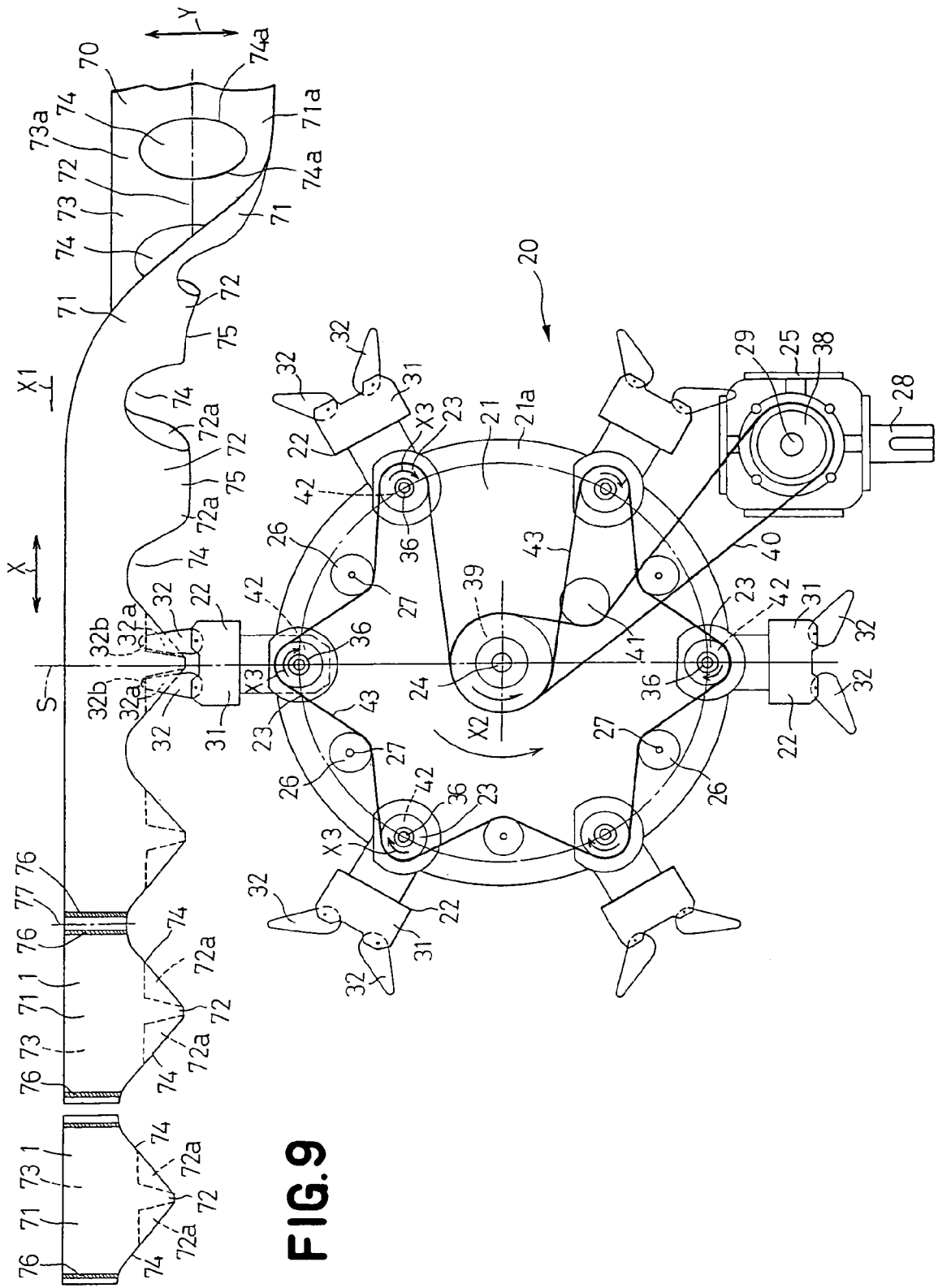
FIG. 9 is an overhead view showing another example of the apparatus for folding and tucking the crotch region.
Figure 10:
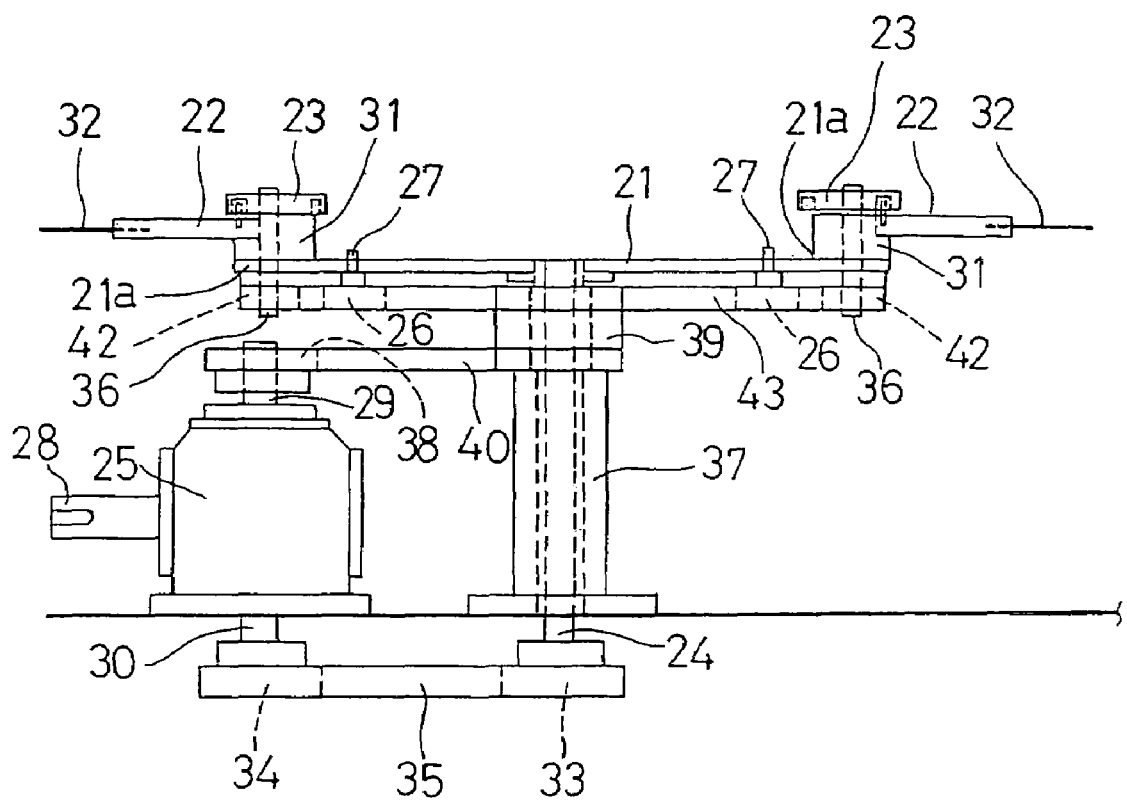
FIG. 10 is a side view corresponding to FIG. 9 showing the apparatus for folding and tucking the crotch region.
Figure 11:
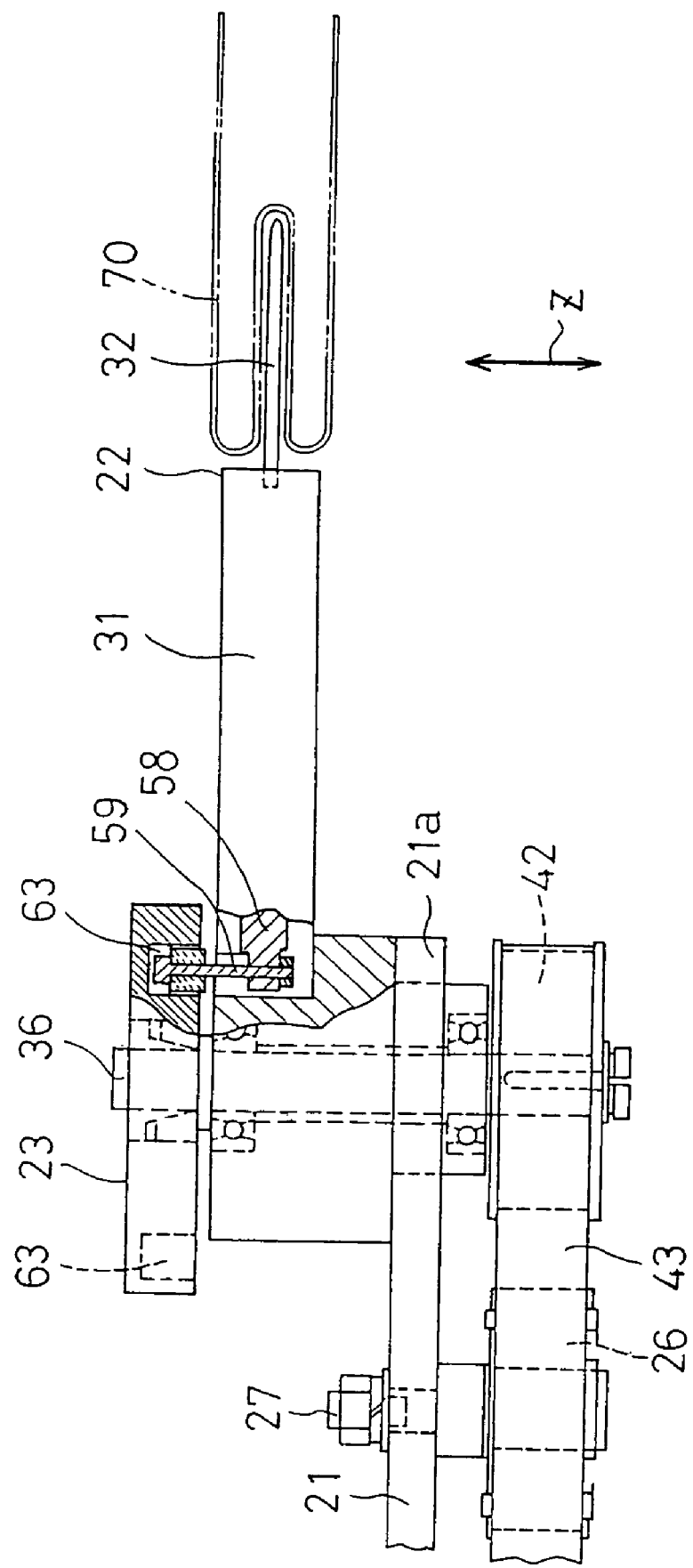
FIG. 11 is a partially cutaway scale-enlarged side view showing a part of FIG. 10.
Figure 12:
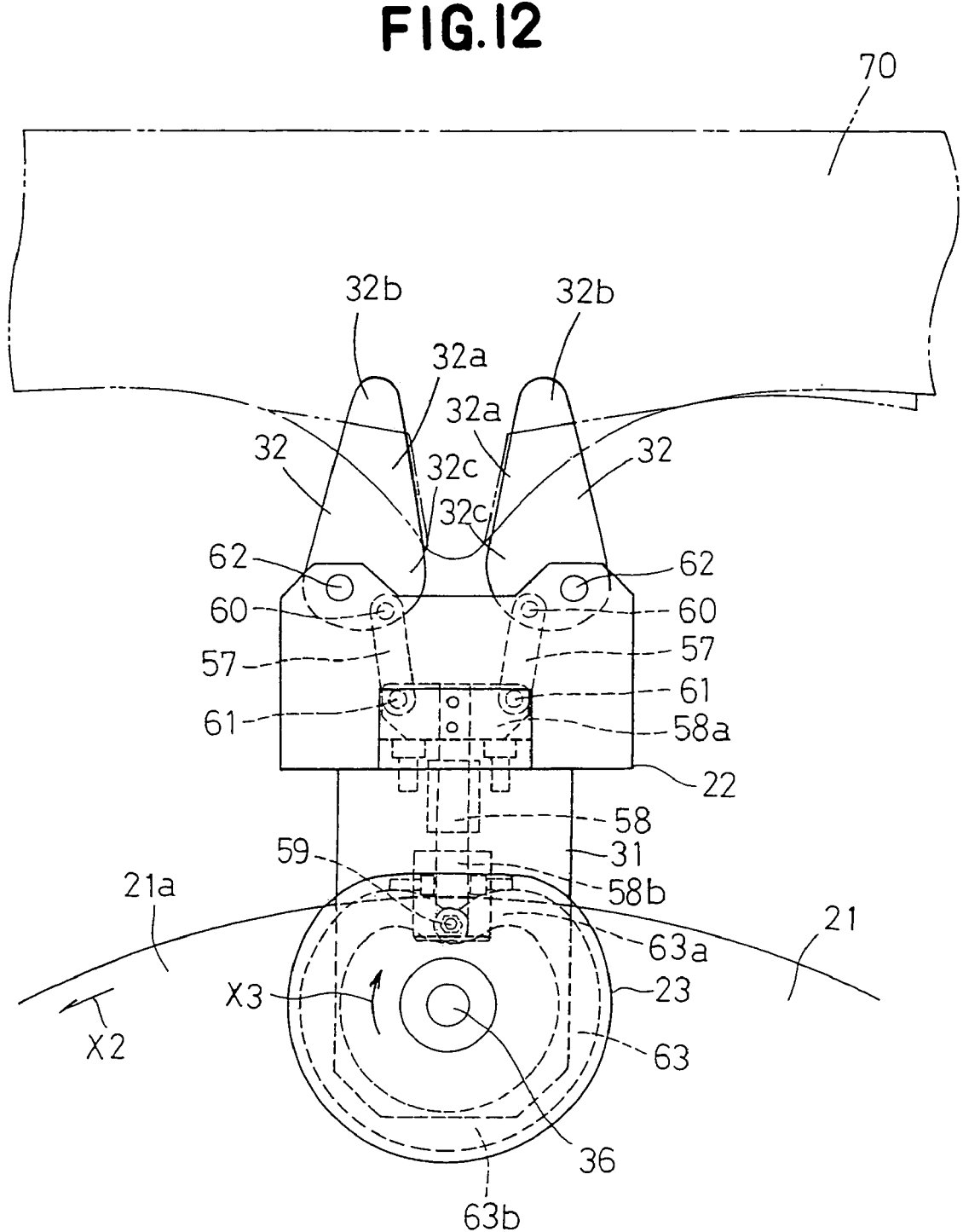
FIG. 12 is a scale-enlarged overhead view of the folding plate.

FIG. 9 is an overhead view showing another example of the apparatus 20 for folding and tucking the crotch region, FIG. 10 is a side view corresponding to FIG. 9 showing the apparatus 20 for folding and tucking the crotch region, FIG. 11 is a scale-enlarged side view showing a part of FIG. 10 as partially cut away and FIG. 12 is a scale-enlarged overhead view of the folding plate 22. In FIG. 9, the machine direction is indicated by the arrow X and the cross direction crossing the machine direction is indicated by the arrow Y. In FIGS. 10 and 11, the vertical direction (i.e., the thickness direction of the contiguous diaper structure 70 folded along the fold 75) is indicated by the arrow Z. In FIG. 12, the guide arms 32 are illustrated as having moved into the diaper structure 70. It should be understood that in FIGS. 9 through 12, illustration of the diaper structure 70 is simplified so that first web and second web can not be distinguished from each other and, the core, the waist elastic members and the leg elastic members are not shown.

The apparatus 20 for folding and tucking the crotch region has a conveyor mechanism (conveyor means) serving to convey the diaper structure 70 at a constant speed forward in the machine direction (in the direction indicated by the arrow X1) and a folding mechanism (folding means) serving to fold down the crotch regions 72 of the diaper structure 70 into this structure 70.

The contiguous diaper structure 70 is similar to that shown in FIG. 4 and has a plurality of crotch regions 72 (corresponding to the crotch region 6) arranged at regular intervals in the machine direction, a plurality of first waist regions 71 (corresponding to the front waist region 5 or the rear waist region 7) and second waist regions 73 (corresponding to the front waist region 5 or the rear waist region 7) lying on both sides of the respective crotch regions 72 in the cross direction and contiguous one to another, in the machine direction, and a plurality of leg-holes 74 each formed between each pair of the adjacent crotch regions 72 and arranged at regular intervals in the machine direction.

The conveyor mechanism conveys the diaper structure 70 forward in the machine direction and, in the course of conveyance, the crotch region 72 is folded along a fold 75 extending in the machine direction so that the first and second waist regions 71, 73 may be opposed to each other but not put flat together (i.e., in a partly opened state).

The diaper structure 70 being conveyed forward in the machine direction is under a predetermined tension exerted thereupon in the machine direction. After the crotch region 72 has been folded along the fold 75, such tension acts on the first and second waist regions 71, 73 but substantially does not act on the crotch region 72.

The folding mechanism comprises a first rotary disc 21 located outside the fold 75 of the diaper structure 70 as viewed in the cross direction, six folding plates 22 mounted at regular intervals on the first rotary disc 21 along its peripheral zone 21a and six positive motion cams 23 overlying the folding plates 22.

The first rotary disc 21 rotates in a direction (indicated by an arrow X2) corresponding to the direction in which the contiguous diaper structure 70 is conveyed about a shaft 24 extending in the vertical direction. Outside the first rotary disc 21, there is provided a gear box 25 adapted to transmit a driving force to the first rotary disc 21 and the folding plates 22. The first rotary disc 21 is provided along its peripheral zone 21a with five guide wheels 26 mounted thereon. The guide wheels 26 are located between each pair of the folding plates 22 adjacent to each other and mounted on the first rotary disc 21 by means of a shaft 27 extending in the vertical direction. These guide wheels 26 are rotatable independently of the first rotary disc 21.

The shaft 28 of the gear box 25 is rotationally driven by an electric motor (not shown). Within the gear box 25, there is provided a bevel gear (not shown) via which a rotation of the shaft 28 is transmitted to a shaft 29 extending upward from the gear box 25 in the vertical direction and a shaft 30 extending downward from the gear box 25.

The folding plates 22 lie outside the fold 75 of the diaper structure 70 as viewed in the cross direction. The folding plates 22 are arranged at regular intervals along the peripheral zone 21a of the first rotary disc 21. The folding plates 22 are adapted to move toward and away from the crotch region 72 of the diaper structure 70 as the first rotary disc 21 rotates. Each of the folding plates 22 comprises the first base 31 and a pair of the guide arms 32 extending outward from the first base 31 in the radial direction of the first rotary disc 21.

Each pair of the guide arms 32 are opposed to each other in a circumferential direction of the first rotary disc 21 and respectively have inner side edges 32a opposed to each other in the circumferential direction of the first rotary disc 21. The guide arms 32 are adapted to swing back and forth so that respective distal ends 32b may repeatedly get near to and get away from each other, that is, so that they repeatedly open and close to each other.

The shaft 24 of the first rotary disc 21 and the shaft 30 of the gear box 25 are provided with the pulleys 33, 34, respectively. These shafts 24, 30 are operatively associated with each other by means of the open belt 35 guided by these pulleys 33, 34. Rotation of the shaft 30 of the gear box 25 is transmitted to the shaft 24 of the first rotary disc 21 via the open belt 35. Rotation of the shaft 30 causes the first rotary disc 21 to rotate in the same direction (indicated by the arrow X2) as the direction in which the shaft 24 rotates.

The positive motion cams 23 overlie the first bases 31 of the respective folding plates 22 and are mounted on the first rotary disc 21 by means of shafts 36 extending in the vertical direction so that these positive motion cams 23 may be rotated independently of the first rotary disc 21. As is the case with the folding plates 22, the positive motion cams 23 are arranged at regular intervals along the peripheral zone 21a of the first rotary disc 21.

The first rotary disc 21 is provided around its bearing 37 with the pulley 39 adapted to rotate independently of the shaft 24. This pulley 39 is rotatably mounted on the bearing 37. The shaft 24 is inserted into the bearing 37. The shaft 29 of the gear box 25 is provided with the pulley 38. The shaft 29 and the pulley 39 are operatively associated with each other via the open belt 40 guided by the pulleys 38, 39. Between the pulley 38 and the pulley 39, there is provided the guide wheel 41 serving to keep the belt 40 under tension. The shafts 36 of the respective positive motion cams 23 are provided with the pulleys 42.

The shaft 36 is operatively associated with the pulley 39 by means of a belt 43 guided by the pulleys 39, 42. More specifically, the belt 43 extends from the pulley 39 to one of the pulleys 42 associated with one of the positive motion cams 23 and further extends, via the guide wheel 26, to the pulley 42 associated with the adjacent positive motion cam 23. Rotation of the shaft 29 is transmitted via the belt 40 to the pulley 39. Rotation of the pulley 39 is transmitted via the belt 43 to the shafts 36 of the positive motion cams 23. Rotation of the shafts 36 causes these positive motion cams 23 to rotate in a direction (indicated by an arrow X3) opposed to the direction (indicated by the arrow X2) in which the first rotary disc 21 rotates. The belt 43 is maintained under tension by the guide wheels 26.

Each of the folding plates 22 has a pair of links 57 mounted on proximal end zones 32c of the guide arms 32, a rod 58 connected to the links 57 and a pin 59 lying in a rear end zone 58b (end zone) of the rod 58 and extending in the vertical direction. The links 57 and the rod 58 extend outward in the radial direction of the first rotary disc 21 from the proximal end zones 32c of the guide arms 32. The links 57 are mounted on shafts 60 provided in the proximal end zones 32c of the guide arms 32 and on shafts 61 lying in a front end zone 58a of the rod 58. The guide arms 32 have the proximal end zones 32c mounted on the first base 31 by means of pivot pins 62.

The positive motion cams 23 respectively have eccentric cam grooves 63. The cam groove 63 includes a depressed zone 63a lying in the peripheral zone of the first rotary disc 21 and sloping down toward the shaft 36 of the cam 23 and a circular zone 63b extending along a peripheral edge of the positive motion cam 23. The pin 59 is slidably inserted into the cam groove 63.

Each of these positive motion cams 23 makes one rotation (360° rotation) about its own axis in the peripheral zone 21a of the first rotary disc 21 while these positive motion cams 23 revolve about the axis of the first rotary disc 21 during one rotation (360° rotation) of the first rotary disc 21 about its own axis. Rotation of the positive motion cams 23 around their own axes causes the pins 59 to move along the cam grooves 63 and thereby causes the rods 58 to move forward and backward in the cross direction. Movement of the rods 58 forward and backward causes the distal ends 32b of the guide arms 32 to be repeatedly got near to and get away from each other by means of the links 57.

The crotch region 72 of the diaper structure 70 is folded and tucked by such apparatus 20 illustrated in FIG. 9 in a manner as follows: The diaper structure 70 having the crotch region 72 folded along the fold 75 extending in the machine direction is being conveyed forward in its machine direction (indicated by the arrow X1) by the conveyor mechanism. The diaper structure 70 with the first and second waist regions 71, 73 opposed to but spaced apart from each other (i.e., in a partly opened state) progressively gets near to the first rotary disc 21. The first rotary disc 21 is rotating in sync with the running speed of the diaper structure 70 in the direction corresponding to the direction in which the diaper structure 70 is conveyed (indicated by the arrow X2).

In the apparatus 20 for folding and tucking crotch regions, the guide arms 32 of the folding plates 22 progressively move from the leg-holes 74 lying on both sides of the crotch region 72 as viewed in the machine direction into the diaper structure 70 as the crotch region 72 of the diaper structure 70 gets near to the peripheral zone 21a of the first rotary disc 21.

As the crotch region 72 of the diaper structure 70 gets near to an imaginary line S extending from the shafts 24 of the first rotary disc 21 in the cross direction, the opposite side edges 32a of the guide arms 32 having moved into the diaper structure 70 come in contact with the crotch region 72 from its outer side and the guide arms 32 swing inward so that the distal ends 32b of the respective guide arms 32 may get close to each other. In this way, the opposite side edges 32a of the guide arms 32 are pressed against the transversely opposite lateral zones 72a of the crotch region 72 extending in the vicinity of the fold 75 so as to compress these lateral zones 72a of the crotch region 72 into the contiguous diaper structure 70, and thereby the lateral zones 72a are tucked into the diaper structure 70.

In the apparatus 20 for folding and tucking crotch regions, the guide arms 32 progressively move backward so as to draw out of the diaper structure 70 and swing so that the distal ends 32b may be spaced from each other as the crotch region 72 of the diaper structure 70 moves away from the peripheral zone 21a of the first rotary disc 21. The diaper structure 70 having the crotch region 72 thus folded and tucked progressively moves away from the first rotary discs 21 and further moves forward in the machine direction.

In the diaper structure 70 having the crotch region 72 folded along the fold 75 extending in the machine direction, the crotch region 72 is substantially free from affection of the tension exerted upon the diaper structure 70, so the lateral zones 72a of the crotch region 72 can be easily tucked and, in addition, the diaper structure 70 can be conveyed forward in the machine direction with the crotch region 72 reliably retained in a tucked state.

After the lateral zones 72a of the crotch region 72 have been tucked inward, the first and second waist regions 71, 73 which have been opposed to each other but spaced apart from each other are now completely put flat together and then the first and second webs are joined together by means of two heat-sealing lines 76 extending in the cross direction. These heat-sealing lines 76 lie in the middle of each leg-opening 74 as viewed in the machine direction so as to extend across the first and second waist regions 71, 73 in the cross direction. Subsequently, the first and second webs are cut along cutting lines 77 each extending in the cross direction between the heat-sealing lines 76. These cutting lines 77 extend across the first and second waist regions 71, 73 in the cross direction. The contiguous diaper structure 70 is cut along the respective cutting lines 77 to obtain a plurality of the individual diapers 1 shown in FIG. 1 which are arranged side by side in the machine direction.

This apparatus 20 for folding and tucking crotch regions allows the crotch region 72 of the diaper structure 70 to be continuously and rapidly folded and tucked inward and further allows the crotch region 72 to be reliably folded and tucked inward since the guide arms 32 are pressed against the lateral zones 72a of the crotch region 70 to compress these lateral zones 72a into the diaper structure 70.

While the positive motion cams 23 are used in the apparatus 20 illustrated in Figures for the purpose of swinging the distal ends 32b of the guide arms 32, it is possible to adopt solenoids for the purpose of swinging the distal ends 32b of the guide arms 32. In this case, moving iron cores of the respective solenoids may be moved apart from each other to swing the guide arms 32 so as to get nearer to each other and the moving iron cores of the respective solenoids may be brought in contact with each other to swing the guide arms 32 so as to get away from each other.

A stock material for the liquid-pervious continuous first web (corresponding to the liquid-pervious topsheet 2) may be selected from the group consisting of a hydrophilic fibrous nonwoven fabric, a hydrophobic fibrous nonwoven fabric having a plurality of perforations and a finely perforated plastic film. A stock material for the liquid-impervious continuous second web (corresponding to the liquid-impervious backsheet 3) may be selected from the group consisting of a hydrophobic fibrous nonwoven fabric, a breathable but liquid-impervious plastic film, a composite nonwoven fabric comprising two or more layers of hydrophobic fibrous nonwoven fabric placed one upon another and a composite sheet comprising a hydrophobic fibrous nonwoven fabric and a breathable but liquid-impervious plastic film laminated upon each other.

A nonwoven fabric may be selected from the group consisting of those obtained by spun lace-, needle punch-, melt blown-, thermal bond-, spun bond-, chemical bond- and air-through-processes. Component fibers of nonwoven fabric may be selected from the group consisting of polyolefine-, polyester- and polyamide-based fibers, core-and-sheath type conjugated fibers and side-by-side type conjugated fibers of polyethylene/polypropylene and polyethylene/polyester.

The core 4 is a mixture of fluff pulp and super-absorbent polymer particles or a mixture of fluff pulp, super-absorbent polymer particles and thermoplastic synthetic resin fibers compressed to a desired thickness. Preferably, the core 4 is entirely covered with a liquid-pervious sheet such as tissue paper or a hydrophilic nonwoven fabric in order to prevent the core 4 from getting out of shape and/or to prevent falling off of the polymer particles. Polymer particles may be selected from the group consisting of starch-based, cellulose-based and synthetic polymer-based particles.

With the apparatus and the method for folding and tucking crotch regions of disposable diaper, the folding plates are utilized to fold and tuck the crotch region in the contiguous diaper structure conveyed in the machine direction into the contiguous diaper structure. Such apparatus allows the crotch regions of the diaper structure to be continuously and rapidly folded and tucked inward.

With the apparatus in which the guide arms of the respective folding plates respectively have their distal ends adapted to swing back and forth in the machine direction, the guide arms are pressed against the opposite lateral zones of the crotch region to compress these lateral zones into the diaper structure and thereby to ensure that the crotch region can be reliably tucked inward.

With the apparatus comprising, in addition to the folding plates, the auxiliary plates, the guide arms move into the clearance between the guide blades of the auxiliary plate as the guide arms of the folding plate swing so that the lateral zones of the crotch region may be held between the guide arms and the guide blades. In this way, the crotch region can be further reliably tucked inward.

With the individual diaper having its crotch region folded and tucked by the apparatus, the wearer experiences no feeding of incompatibility as the crotch region is properly received by the wearer's crotch region as the diaper is put on the wearer's body and, even if the crotch region is squeezed by the wearer's crotch region, it is not likely that the crotch region might be irregularly folded and/or the core might be formed with a plurality of irregular creases, and therefore there is no anxiety that the bodily discharge absorbing capacity in the crotch region might be deteriorated.

With this diaper is free from the inconvenience that the wearer's toes and/or heels might get stuck on the lateral zones of the crotch region as the wearer's legs are guided through the waist-hole and then through the leg-holes to put the diaper on the wearer's body, and therefore the diaper can be smoothly put on the wearer's body.

What is claimed is:

1. An apparatus for folding and tucking crotch regions of disposable diapers, said apparatus comprising:

a conveyor mechanism for conveying a contiguous diaper structure, said contiguous diaper structure having a plurality of crotch regions arranged at regular intervals in a machine direction, a plurality of first and second waist regions lying on both sides of said crotch regions as viewed in a cross direction orthogonal to said machine direction and lying contiguous one to another in said machine direction, and a plurality of leg-holes each formed between one pair of said crotch regions adjacent to each other, and said leg-holes being arranged at regular intervals in the machine direction, wherein said contiguous diaper structure is adapted to be folded, while being conveyed by said conveyor mechanism, along a fold in said crotch regions so that said first and second waist regions are opposed to but spaced apart from each other; and a folding mechanism for folding and tucking each said crotch region of said contiguous diaper structure from said leg-holes lying on both sides of said crotch region toward an inside of said folded contiguous diaper structure;

said folding mechanism including a first rotary disc located outside said fold in said crotch regions as viewed in said cross direction and adapted to rotate, about a first axis extending in a thickness direction of said diaper structure, in a direction in which said diaper structure is conveyed, and a plurality of folding plates arranged on said first rotary disc in a peripheral zone of said first rotary disc at regular intervals in a circumferential direction of said first rotary disc and adapted to approach and then move away from said crotch regions as said first rotary disc rotates;

each of said folding plates comprising a first base, and a pair of guide arms arranged in said circumferential direction of said first rotary disc and extending radially outward from said peripheral zone of said first rotary disc; and as said first rotary disc rotates, said folding plates being adapted to revolve around said first axis of said first rotary disc, said guide arms being adapted to (i) move forward progressively from a side of the respective crotch region so as to go to the inside of said folded diaper structure as said crotch region of said folded diaper structure approaches said peripheral zone of said first rotary disc so that opposite side edges of said guide arms are pressed against transversely opposite side edges of said crotch region in a vicinity of said fold from outside so as to compress said opposite side edges into the inside of said contiguous folded diaper structure, and (ii) subsequently move backward progressively so as to draw out of said folded diaper structure as said crotch region moves away from the peripheral zone of said first rotary disc.

2. The apparatus according to claim 1, wherein said guide arms are adapted to repeatedly swing back and forth in said machine direction so that distal ends of said guide arms repeatedly approach and move away from each other; and said opposite side edges of said guide arms are adapted to progressively approach each other as said guide arms move forward so as to go to the inside of said folded diaper structure and progressively move away from each other as said guide arms move backward so as to draw out of said folded diaper structure.

3. The apparatus according to claim 1, wherein:

said folding mechanism further includes a plurality of positive motion cams arranged at regular intervals in said circumferential direction along the peripheral zone of said first rotary disc and rotatably mounted on said first rotary disc by means of shafts extending in said thickness direction of said diaper structure;

each of said folding plates has links mounted on proximal ends of said guide arms, a rod connected to said guide arms by means of said links, and a pin extending in said thickness direction of said diaper structure from an end of said rod lying adjacent said first base wherein said pin is slidably inserted into an eccentric cam groove of said respective positive motion cam;

said positive motion cams are adapted to revolve about the first axis of said first rotary disc as said first rotary disc rotates around said first axis, each said positive motion cams is also rotatable about its own axis and adapted to make one full 360° rotation about its own axis located in the peripheral zone of said first rotary disc while said first rotary disc makes one full 360° rotation about the first axis, and movement of said pin along said cam groove causes said rod to move forward and backward in said cross direction and thereby causes said respective guide arms to swing so that said distal ends thereof repeatedly approach and move away from each other.

4. The apparatus according to claim 1, wherein:

said folding mechanism further includes a second rotary disc located on a side opposite to said first rotary disc across said diaper structure and adapted to rotate, around a second axis extending in said thickness direction of said diaper structure, in said direction in which said diaper structure is conveyed, and a plurality of auxiliary plates mounted on said second rotary disc along a peripheral zone of said second rotary disc at regular intervals in a circumferential direction of said second rotary disc and adapted to approach and move away from said crotch regions as said second rotary disc rotates;

each of said auxiliary plates comprises a second base, and a pair of guide blades arranged one on top the other in said thickness direction of said diaper structure and extending radially outward from the peripheral zone of said second rotary disc, wherein said guide blades have distal ends tapered outward radially of said second rotary disc; and as said second rotary disc rotates, said auxiliary plates are adapted to revolve about said second axis of said second rotary disc, said guide blades are adapted to (i) move forward progressively so as to go into the inside of said folded diaper structure through a clearance defined between said first and second waist regions in synchronization with said guide arms, as said crotch region of said folded diaper structure approaches a space defined between said first and second rotary discs, so that said guide arms simultaneously move into a spacing defined between said guide blades and said transversely opposite lateral zones of said crotch region are held between said guide arms and said guide blades and thereby tucked inwardly of said contiguous folded diaper structure, and (ii) then move away from said folded diaper structure as said crotch region of said diaper structure leaves the space defined between said first and second rotary discs.

5. The apparatus according to claim 1, wherein said continuous diaper structure comprises a liquid-pervious continuous first web, a liquid-impervious continuous second webs, and a plurality of liquid-absorbent cores interposed between said first and second webs and extending in said cross direction over the respective crotch regions further into said first and second waist regions.

6. A method of folding and tucking crotch regions, said method comprising the steps of:

conveying a continuous diaper structure having a plurality of crotch regions arranged at regular intervals in a machine direction, a plurality of first and second waist regions lying on both sides of said crotch regions as viewed in a cross direction orthogonal to said machine direction and being continuous one to another in said machine direction, and a plurality of leg-holes each formed between one pair of said crotch regions adjacent to each other, and said leg-holes being arranged at regular intervals in said machine direction;

folding, during said conveying, said diaper structure along a fold in said crotch regions so that said first and second waist regions are opposite to but spaced apart from each other; and folding and tucking each said crotch region of said continuous diaper structure from said leg-openings lying on both sides of said crotch region toward an inside of said contiguous folded diaper structure;

wherein the step of folding and tucking includes rotating a first rotary disc located outside said fold in said crotch regions as viewed in said cross direction, about a first axis extending in a thickness direction of said diaper structure, in a direction in which said diaper structure is conveyed, causing a plurality of folding plates arranged on said first rotary disc in a peripheral zone of said first rotary disc at regular intervals in a circumferential direction of said first rotary disc to approach and then move away from said crotch regions as said first rotary disc rotates;

each of said folding plates comprising a first base, and a pair of guide arms arranged in said circumferential direction of said first rotary disc and extending radially outward from the peripheral zone of said first rotary disc; and as said first rotary disc rotates, revolving said folding plates about said first axis of said first rotary disc, moving said guide arms forward progressively from a side of said respective crotch region so that said guide arms go into the inside of said folded diaper structure as said crotch region of said folded diaper structure approaches the peripheral zone of said first rotary disc so that opposite side edges of said guide arms are pressed against transversely opposite side edges of said crotch region in a vicinity of said fold from outside so as to compress said opposite side edges into the inside of said contiguous folded diaper structure, and subsequently moving said guide arms backward progressively so that said guide arms draw out of said folded diaper structure as said crotch region moves away from the peripheral zone of said first rotary disc.

7. The method according to claim 6, further including the step of swinging said guide arms back and forth repeatedly in said machine direction so that distal ends of said guide arms repeatedly approach and move away from each other; and causing said opposite side edges of said guide arms to approach each other progressively as said guide arms move forward so as to go to the inside of said folded diaper structure and move away from each other progressively as said guide arms move backward so as to draw out of said folded diaper structure.

8. The method according to claim 6, wherein the step of folding and tucking further includes rotating a plurality of positive motion cams arranged at regular intervals in said circumferential direction along the peripheral zone of said first rotary disc and rotatably mounted on said first rotary disc by means of shafts extending in said thickness direction of said diaper structure;

each of said folding plates having links mounted on proximal ends of said guide arms, a rod connected to said guide arms by means of said links, and a pin extending in said thickness direction of said diaper structure from an end of said rod lying adjacent said first base wherein said pin is slidably inserted into an eccentric cam groove of said respective positive motion cam;

revolving said positive motion cams about said first axis of said first rotary disc as said first rotary disc rotates around said first axis, while rotating each of said positive motion cams a full 360° once about its own axis located in the peripheral zone of said first rotary disc while said first rotary disc makes one full 360° rotation about said first axis, and moving said pin along said cam groove to cause said rod to move forward and backward in said cross direction and thereby said guide arms to swing so that said distal ends thereof repeatedly approach and move away from each other.

9. The method according to claim 6, wherein:

the step of folding and tucking further includes rotating a second rotary disc located on a side opposite to said first rotary disc across said diaper structure, around a second axis extending in said thickness direction of said diaper structure, in said direction in which said diaper structure is conveyed, causing a plurality of auxiliary plates mounted on said second rotary disc along a peripheral zone of said second rotary disc at regular intervals in a circumferential direction of said second rotary disc to approach and draw away from said crotch regions as said second rotary disc rotates;

each of said auxiliary plates comprising a second base, and a pair of guide blades arranged one on top the other in said thickness direction of said diaper structure and extending radially outward from the peripheral zone of said second rotary disc, wherein said guide blades have distal ends tapered outward radially of said second rotary disc; and as said second rotary disc rotates, revolving said auxiliary plates about the second axis of said second rotary disc, moving said guide blades progressively forward so as to go into the inside of said folded diaper structure through a clearance defined between said first and second waist regions in synchronization with said guide arms, as said crotch region of said folded diaper structure approaches a space defined between said first and second rotary discs, so that said guide arms simultaneously move into a spacing defined between said guide blades and said transversely opposite lateral zones of said crotch region are held between said guide arms and said guide blades and thereby tucked inwardly of said contiguous folded diaper structure, and then moving said guide blades progressively away from said folded diaper structure as said crotch region of said diaper structure leaves said space defined between said first and second rotary discs.

10. The method according to claim 6, wherein said continuous diaper structure comprises a liquid-pervious continuous first web, a liquid-impervious continuous second web, and a plurality of liquid-absorbent cores interposed between said first and second webs and extending in said cross direction over the respective crotch regions further into said first and second waist regions.

* * * * *